(12) United States Patent
Cohan et al.

(10) Patent No.: US 7,133,712 B2
(45) Date of Patent: Nov. 7, 2006

(54) METHOD AND APPARATUS FOR NON-INVASIVE MONITORING OF BLOOD SUBSTANCES USING SELF-SAMPLED TEARS

(75) Inventors: Bruce E. Cohan, Ann Arbor, MI (US); Geun Sig Cha, Seoul (KR); Mark E. Meyerhoff, Ann Arbor, MI (US); Hakhyun Nam, Seoul (KR); Donald E. Gillespie, Ann Arbor, MI (US); Gang Cui, Jilin (CN); Jong Sik Kim, Seoul (KR); Zvi Flanders, Ann Arbor, MI (US)

(73) Assignee: Eyelab Group, LLC, Ann Arbor, MI (US)

( * ) Notice: Subject to any disclaimer, the term of this patent is extended or adjusted under 35 U.S.C. 154(b) by 392 days.

(21) Appl. No.: 10/404,702

(22) Filed: Apr. 1, 2003

(65) Prior Publication Data

US 2003/0211625 A1 Nov. 13, 2003

Related U.S. Application Data

(60) Provisional application No. 60/370,552, filed on Apr. 5, 2002.

(51) Int. Cl.
*A61B 5/00* (2006.01)
*A61B 5/05* (2006.01)

(52) U.S. Cl. .................. 600/345; 600/347; 600/365
(58) Field of Classification Search .............. None
See application file for complete search history.

(56) References Cited

U.S. PATENT DOCUMENTS

| 4,994,751 A | 2/1991 | Cook et al. |
| 5,047,206 A * | 9/1991 | Dombrowski ............... 422/56 |
| 5,140,985 A | 8/1992 | Schroeder et al. |
| 5,352,411 A * | 10/1994 | Khuri ........................ 422/58 |
| 5,854,078 A | 12/1998 | Asher et al. |
| 5,898,004 A | 4/1999 | Asher et al. |
| 6,151,522 A | 11/2000 | Alfano et al. |
| 6,187,599 B1 | 2/2001 | Asher et al. |
| 6,267,722 B1 | 7/2001 | Anderson et al. |
| 6,312,393 B1 | 11/2001 | Abreu |
| 6,544,800 B1 | 4/2003 | Asher |
| 6,773,564 B1 * | 8/2004 | Yugawa et al. ........ 204/403.14 |
| 2003/0027240 A1 | 2/2003 | Asher et al. |
| 2003/0106809 A1 * | 6/2003 | Kermani et al. ............ 205/775 |
| 2003/0176183 A1 * | 9/2003 | Drucker et al. ........... 455/414.1 |
| 2004/0249310 A1 * | 12/2004 | Shartle et al. .............. 600/583 |

OTHER PUBLICATIONS

Van Haeringen et al, "Collection Method Dependant Concentrations of Some Metabolites in Human Tear Fluid, with Special reference to Glucose Hyperglycemic Conditions," Albrecht von Grafes Arch., Klin Ophthamologie, 2002:1-7, 1977.*

(Continued)

*Primary Examiner*—Robert L. Nasser
(74) *Attorney, Agent, or Firm*—Brooks Kushman P.C.

(57) ABSTRACT

A method and apparatus for non-invasively determining the concentration of a substance in blood, such as glucose, include a sample portion arranged for contacting an eye region of a user to obtain a tear fluid sample, a sensor in communication with the sample portion for generating a signal related to the tear substance concentration, and a processor in communication with the sensor for determining a blood substance concentration corresponding to the tear substance concentration.

52 Claims, 6 Drawing Sheets

OTHER PUBLICATIONS

Ramano et al, "A non-invasive Method of Blood Glucose Evaluation by Tear Glucose Measurement, for detection and Control of Diabetic State," Metabolic, Pediatric, and Systemic Opthamology, 11:78-80, 1988.*

The Effect of Intensive Treatment of Diabetes on the Development and Progression of Long-Term Complications in Insulin-Dependent Diabetes Mellitus, The New England Journal of Medicine, 1993, vol. 329, No. 14, pp. 977-986.

Philip E. Cryer, Hypoglycemia: The Limiting Factor in the Management of IDDM, Diabetes, vol. 13 Nov. 1994, pp. 1378-1389.

Rong Chen et al., Analysis of Tear Fluid by CE/LIF: A noninvasive Approach for Glucose Monitoring, J. Cap. Elec. 003:5, 1996, pp. 243-248.

J. Martin Bland et al., Statistical Methods for Assessing Agreement Between Two Methods of Clinical Measurement, THE LANCET, Feb. 8, 1986, pp. 307-310.

Maureen I. Harris et al., Prevalence of Diabetes, Impaired Fasting Glucose, and Impaired Glucose Tolerance in U.S. Adults, DIABETES CARE, vol. 21, No. 4, Apr. 1988, pp. 518-524.

Natalie S. Schwartz et al., Glycemic Thresholds for Activation of Glucose Counterregulatory Systems Are Higher than the Threshold of Symptoms, J. Clin. Invest., vol. 79, Mar. 1987, pp. 777-781.

D. Liu et al., Arterial, Arterialized Venous, Venous and Capillary Blood Glucose Measurements in Normal Man During Hyperinsulinaemic Euglycaemia and Hypoglycaemia, Diabetologia (1992), 35, pp. 287-290.

Z. Trajanoski et al., Accuracy of Home Blood Glucose Meters During Hypoglycemia, DIABETES CARE, vol. 19, No. 12, Dec. 1996, pp. 1412-1415.

Dietmar Stockl et al., Evaluating Clinical Accuracy of Systems for Self-Monitoring of Blood Glucose by Error Grid Analysis, DIABETES CARE, vol. 23, No. 11, Nov. 2000, pp. 1711-1712.

Glucose Sensors: Device Approved for Children; Others in Pipeline, pp. 1-3, 2001 http://216.167.3.245/research/feature/res091102b.php.

* cited by examiner

METHOD AND APPARATUS FOR NON-INVASIVE MONITORING OF BLOOD SUBSTANCES USING SELF-SAMPLED TEARS

CROSS-REFERENCE TO RELATED APPLICATIONS

This application claims the benefit of U.S. provisional application Ser. No. 60/370,552 filed Apr. 5, 2002.

BACKGROUND OF THE INVENTION

1. Field of the Invention

This invention relates to a method and apparatus for non-invasive monitoring of blood substances, particularly glucose, using self-sampled tears.

2. Background Art

The measurement of glucose in blood plasma is perhaps the most important physiologic analyte measurement in medicine, as diabetes has immense public health implications. Diabetes is a leading cause of disability and death, affecting approximately seventeen million Americans. The total annual cost of treating diabetes and its complications in the United States is in excess of $150 billion, a large part of the total national expenditure for health care.

The medical management of diabetes by tight glycemic (blood glucose) control can minimize its devastating kidney, ocular, neurological, and vascular complications, as documented in the National Institutes of Health-sponsored Diabetes Control and Complications Trial. However, the trial resulted in a three-fold increase in hypoglycemic incidents. Of great concern to diabetologists in their care of these patients is hypoglycemia awareness because of its serious risk for morbidity and mortality.

Tight glycemic control requires frequent measurement by the patient of his/her blood glucose levels, which typically requires a "finger stick" to obtain a blood sample up to eight times daily. This procedure is painful and inconvenient for even the most compliant patients, such that limited patient compliance with self-testing is a significant problem in the medical management of this disease. Accordingly, the need for a non-invasive approach to diabetes management is universally recognized to achieve the goal of involving patients in a proactive way in their glycemic control, both in monitoring blood glucose and in insulin delivery.

The tremendous need for a reliable, cost-effective method of non-invasive blood glucose measurement for diabetes management has stimulated hundreds of analytic approaches. The invasiveness of these approaches extends from implanted sensors through a range of less, to minimally, to non-invasive methods. Minimally invasive methods include chemical or spectroscopic measurement of interstitial fluid from the skin obtained by reverse iontophoretic, electroosmotic, or thermal microporation sampling. Among the other technologically sophisticated approaches to glucose measurement are spectroscopy (transcutaneous infrared, fluorescence lifetime, pulsed laser photoacoustic, and far infrared), analysis of breath, optical measurements of the aqueous humor of the eye, polarimetry, and radio wave impedance. Some of these methods have worked well in controlled laboratory testing, but in practice other chemical species, tissue optics, variations in temperature, and other factors have confounded the measurement. For all spectroscopic approaches, the major problem is the need for frequent calibration, as infrared absorption bands for various chemicals in blood or interstitial fluid can overlap significantly and are influenced by temperature and hydrogen bonding effects.

The concentration of low molecular weight analytes, like glucose, in blood plasma is correlated with the levels found in lacrimal fluid, or tears. While a number of methods for measuring this analyte have been applied to tears, two main factors have prevented the practical use of measuring tear glucose concentration as a means for self-monitoring blood glucose concentration: 1) the low level of glucose in tears, reported in a recent study (see Chen et al., J Cap Elec 1996; 5:243–248) to be approximately ⅕ the level in blood, and 2) the small volume of tear fluid as compared with blood that is readily available for analysis. In the aforementioned Chen study, glucose concentration in microliter samples of human tears obtained with capillary tubes was determined by capillary electrophoresis (CE) with laser-induced fluorescence (LIF), a sophisticated method limited to research chemistry laboratories because of its technical complexity.

Currently, no practical, entirely non-invasive system and method exists for patients to self-monitor their blood glucose with the level of accuracy and responsiveness required.

SUMMARY OF THE INVENTION

Therefore, it is an object according to the present invention to provide a method and apparatus for determining the concentration of a substance in tears which will allow for indirect monitoring of the substance concentration in blood.

It is a further object according to the present invention to provide an improved method and apparatus for non-invasively determining blood glucose concentration in a simple and accurate manner.

It is a still further object according to the present invention to provide a method and apparatus for determining glucose concentration in tear fluid that is self-sampled by a patient.

Accordingly, a method is provided for determining the concentration of a substance in blood, such as glucose, where the method includes providing a test apparatus having a sample inlet, and engaging an eye region of a user with the sample inlet to obtain a tear fluid sample. The method further includes processing the tear fluid sample using the test apparatus to determine a tear substance concentration, and correlating the determined tear substance concentration with a blood substance concentration.

Correspondingly, an apparatus for determining the concentration of a substance in blood, such as glucose, is provided which includes a sample portion arranged for contacting an eye region of a user to obtain a tear fluid sample, a sensor in communication with the sample portion for generating a signal related to the tear substance concentration, and a processor in communication with the sensor for determining a blood substance concentration corresponding to the tear substance concentration.

In a preferred embodiment, a user self-samples tear fluid from his/her eye region by engaging a lower lid region and obtaining tear fluid from a tear meniscus. While obtaining the tear fluid sample, the eye may be substantially closed. Advantageously, the tear fluid sample can be less than about 0.5 μL. Preferably, the sample portion, or test probe, includes an inlet that extends outwardly from the test probe, such as a capillary member or a wicking membrane, to facilitate contact with the eye. The sample portion is preferably removable from the apparatus. In a preferred embodiment, the apparatus includes a generally pen-shaped housing.

The sample portion includes an enzyme, preferably glucose dehydrogenase, for reacting with the substance in the tear fluid sample. The sample portion further includes an electron transfer mediator, such as a ruthenium complex. The coenzyme pyrrolo-quinoline-quinone (PQQ) can also be utilized. In a preferred embodiment, the sample portion includes a base plate, a cover plate, and a spacer disposed between and joining the base and cover plates, where the base and cover plates include a converse-type electrode system. A power supply is provided for applying a voltage to the electrode system to induce an electrochemical reaction of the enzyme and the electron transfer mediator with the substance in the tear fluid sample and generate a current related to the tear substance concentration. The processor then determines a tear glucose concentration from the generated current and multiplies the tear glucose concentration by a calibration factor to determine the corresponding blood glucose concentration. An amplifier can be provided for amplifying the generated current, and a speaker can be provided to generate audible indications for the user. Additionally, a display screen is provided in communication with the processor for displaying the blood substance concentration, and memory is provided in communication with the processor for storing the blood substance concentration.

In accordance with the present invention, a method for determining glucose concentration in a sample of tear fluid includes providing a test apparatus having a sample inlet arranged for contacting an eye region of a user, engaging the eye region with the sample inlet to obtain a tear fluid sample, and processing the tear fluid sample using the test apparatus to determine the glucose concentration in the tear fluid sample. Correspondingly, an apparatus for determining glucose concentration in a tear fluid sample includes a sample portion arranged for contacting an eye region of a user to obtain a tear fluid sample, a sensor in communication with the sample portion for generating a signal related to the glucose concentration in the tear fluid sample, and a processor in communication with the sensor for processing the signal to determine the tear glucose concentration.

In further accordance with the present invention, a method for determining blood glucose concentration includes providing a test apparatus including a sample portion which includes an enzyme. The method further includes engaging an eye region of a user with the sample portion to obtain the tear fluid sample, reacting the tear fluid sample with the enzyme to generate a signal related to the tear glucose concentration, processing the signal using the test apparatus to obtain a blood glucose concentration corresponding to the tear glucose concentration, and providing an output indicative of the blood glucose concentration. Correspondingly, an apparatus for determining glucose concentration in blood includes a sample portion having an inlet arranged for contacting an eye region of a user to obtain a tear fluid sample, where the sample portion contains an enzyme for initiating a reaction with the tear fluid sample. A sensor in communication with the sample portion detects a signal generated by the reaction, and a processor in communication with the sensor determines a tear glucose concentration from the detected signal and correlates the determined tear glucose concentration with a blood glucose concentration. The apparatus further includes means for providing an output indicative of the blood glucose concentration.

According to the present invention, a probe is provided for obtaining a tear fluid sample. The probe includes an input end arranged to contact an eye region of a user to obtain the tear fluid sample, and a probe body in communication with the input end and having components for generating a reaction with a substance, such as glucose, in the tear fluid sample. The probe further includes an output end in communication with the probe body and arranged to be removably mated with a test apparatus for determining a concentration of the substance in the tear fluid sample.

In a preferred embodiment, the input end extends outwardly from the probe body, and can include a capillary member or a wicking membrane. The probe body preferably includes an enzyme, such as glucose dehydrogenase, for reacting with the substance in the tear fluid sample, and can also include a coenzyme, such as pyrrolo-quinoline-quinone (PQQ). The probe body preferably further includes an electron transfer mediator, such as a ruthenium complex. The probe body preferably includes a base plate, a cover plate, and a spacer disposed between and joining the base and cover plates, where the base and cover plates include an electrode system. The electrode system is of a converse type, where a working electrode is provided on one of the base and cover plates and a reference electrode is provided on the other of the base and cover plates.

The above objects and other objects, features, and advantages of the present invention are readily apparent from the following detailed description of the best mode for carrying out the invention when taken in connection with the accompanying drawings.

DETAILED DESCRIPTION OF THE PREFERRED EMBODIMENT(S)

The method and apparatus of the present invention provide for the practical, non-invasive determination of the concentrations of substances, particularly glucose, in human tears in order to indirectly monitor the level of this important analyte in blood. The method and apparatus described herein are designed for the special limitations of analysis of tear fluid, namely the low glucose concentration in tears compared with blood and the small sample volume available. The present invention advances tight glycemic control of diabetes by permitting users to monitor their blood glucose levels by self-measuring the glucose levels in their tears, wherein the tear fluid sample is easily obtained by a user and accurate results are immediately available.

By way of background, the primary aqueous component of tears is secreted by the lacrimal gland, which is located beneath the outer portion of the upper eyelid. In this gland, a fraction of the glucose in blood crosses into the tears. This fluid flows from the gland through a number of tiny lacrimal gland ducts onto the surface of the eye where it forms a thin layer that maintains a wet, optically smooth corneal surface, and lubricates with moisture the conjunctiva, the mucous membrane which covers the sclera and lines the lids, joining under the upper and lower lids in a cul de sac. The tear fluid is continually secreted and flows across the eye at a rate of about 2 µl per minute. The tears form a meniscus along the lower lid margin and a shallow pool, the lacrimal lake, between the inner (nasal) edge of the cornea and near the joining of the lids nasally. The total volume of lacrimal fluid on the surface of the eye is about 7 µl. A small opening, the lacrimal punctum, near the nasal end of each lid opens into a tubular channel, the lacrimal canaliculus, which drains the tears into the lacrimal sac. From there, the lacrimal fluid empties into the nose.

Figure 1A:
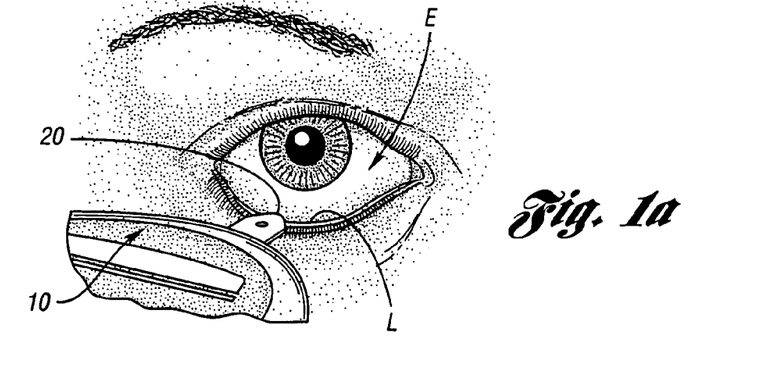
FIGS. 1a and 1b are photographs of front and side views, respectively, of a user self-sampling tears according to the present invention.
Figure 1B:
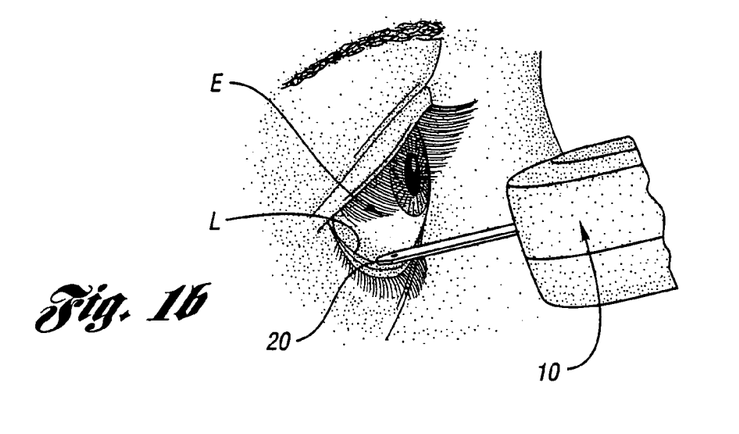

With reference first to FIGS. 1$a$ and 1$b$, photographs of a user conducting self-sampling of tear fluid are shown. According to the present invention, a user self-samples his/her tear fluid as follows. The user places a sample inlet of a test apparatus 10, described below with reference to FIGS. 2–8, in contact with his/her eye region E, preferably at the lower lid margin L. To aid in this procedure, the user may exert gentle traction with his/her finger on the skin of the lower lid, as is typically done for inserting contact lenses, and may view the procedure in a mirror. Tear fluid is then obtained from the tear meniscus along the lower lid margin L, and the sample drawn up into the test apparatus 10 by capillary action without requiring any intermediate handling of tears. Tears can also be self-sampled from the lateral canthal region and from the lacrimal lake. It is understood that the test apparatus 10 need not necessarily engage the eye itself, but simply engage the eye region E sufficiently to obtain the tear fluid sample. Furthermore, the tear fluid sample need not be self-obtained by the user, but could be sampled from the user by another individual. In order to stabilize glucose concentrations across the eye, a user may substantially close his/her eye in order to perform the self-sampling procedure according to the present invention. Due to the small sample volume (<0.5 µl) required by the method and apparatus of the present invention, there is no need to induce tearing to obtain the tear fluid sample.

Figure 2:
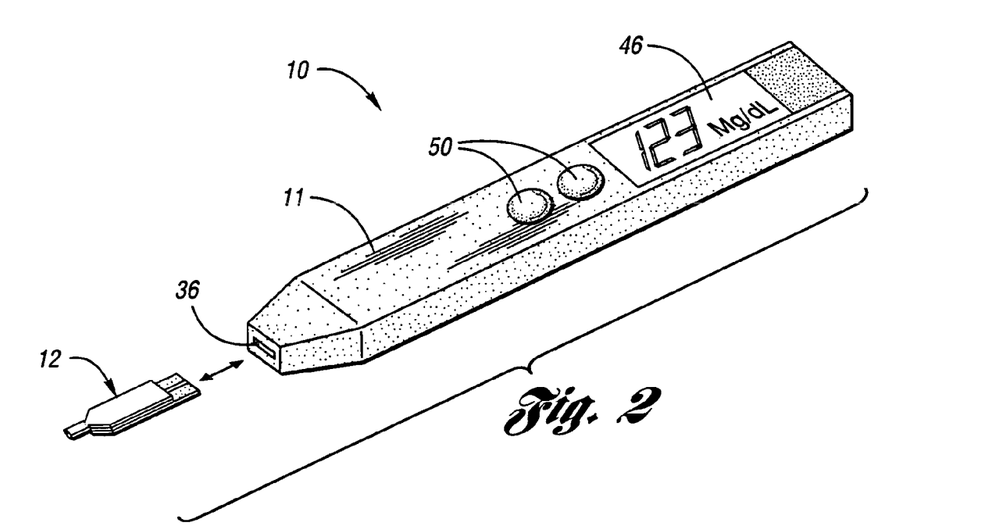
FIG. 2 is a perspective view of a preferred embodiment of the test apparatus of the present invention, wherein the test probe is shown in a removed position.
Figure 3:
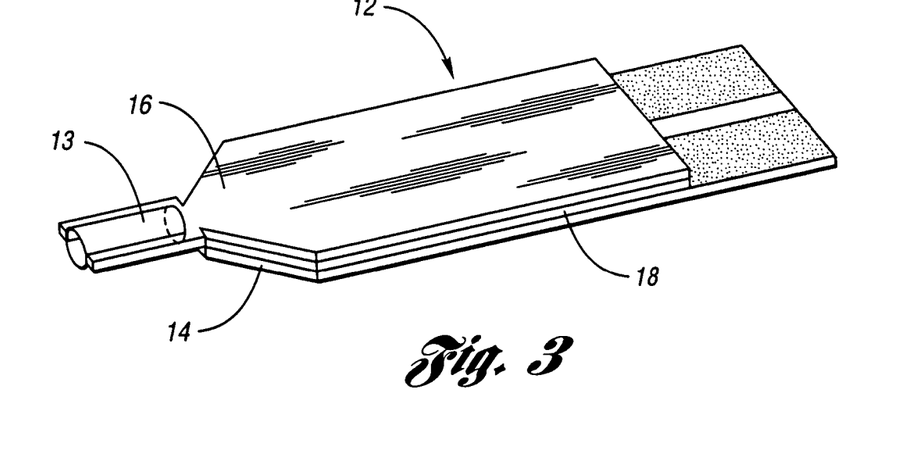
FIG. 3 is a perspective view of the test probe of FIG. 2.

Turning now to FIGS. 2–8, the test apparatus 10 according to the present invention will now be described. Advantageously, test apparatus 10 provides the means for obtaining the tear fluid sample as well as the means for analyzing the glucose concentration of the tear fluid sample. With reference to FIG. 2, a preferred embodiment of the test apparatus 10 is shown, wherein test apparatus 10 includes a sample probe, preferably an electrochemical test probe 12 as shown and described herein. Test apparatus 10 preferably comprises a generally pen-shaped housing 11 for ease of manipulation by the user while obtaining the tear fluid sample.

As is known in the art for blood glucose analysis, the test probe 12 contains chemicals for measuring glucose concentration by determining the product of an enzymatic reaction, wherein the selectivity of the enzyme allows for discrimination between glucose and other substances. In a preferred embodiment, test probe 12 is constructed similar to that described in International Application No. PCT/KR02/00703 published on Jul. 10, 2003, which is incorporated by reference herein. However, in the present invention, the test probe 12 does not require a blood sample from a user, but instead accepts a tear fluid sample for analysis of glucose concentration. Test probe 12 generally includes an input end for obtaining the tear fluid sample, a probe body for reacting the tear fluid sample, and an output end for communicating with test apparatus 10 as described below. Although an electrochemical test apparatus 10 is shown and described herein, it is understood that a test apparatus using another analytical technique (e.g., fluorescence, absorbance) capable of accurately determining the concentration of glucose in tear fluid could alternatively be utilized in accordance with the present invention.

Figure 4:
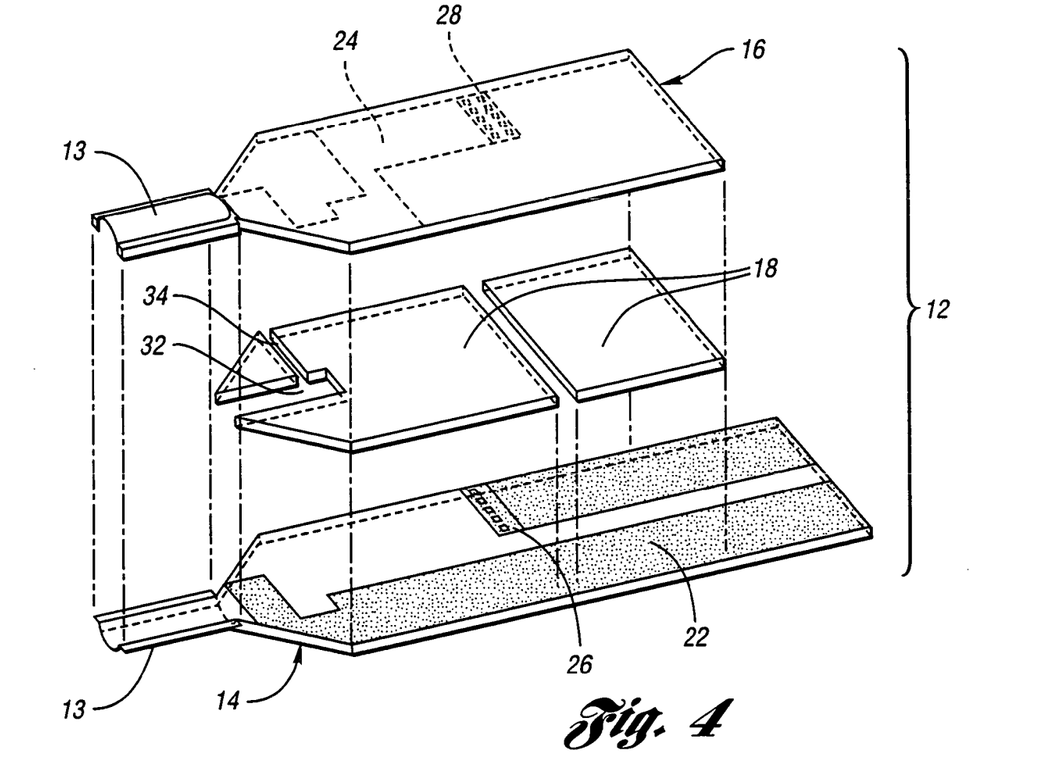
FIG. 4 is an exploded perspective view of the test probe of FIG. 3.
Figure 5:
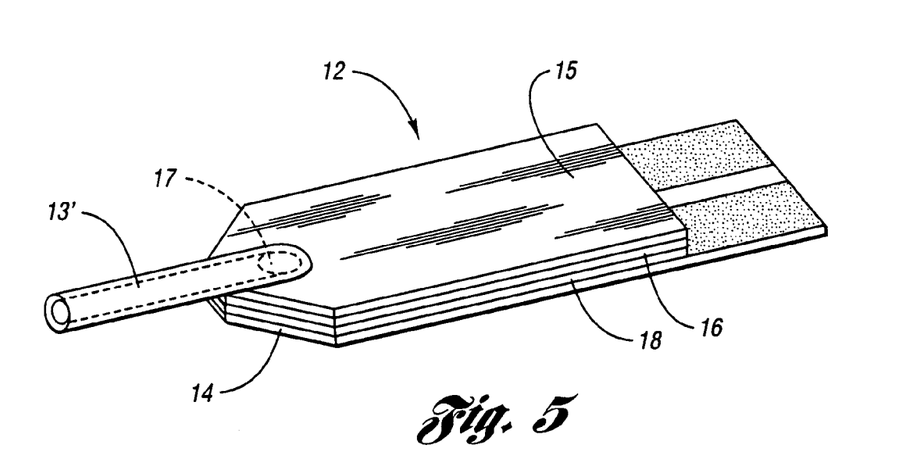
FIG. 5 is a perspective view of an alternative embodiment of the test probe according to the present invention.
Figure 6:
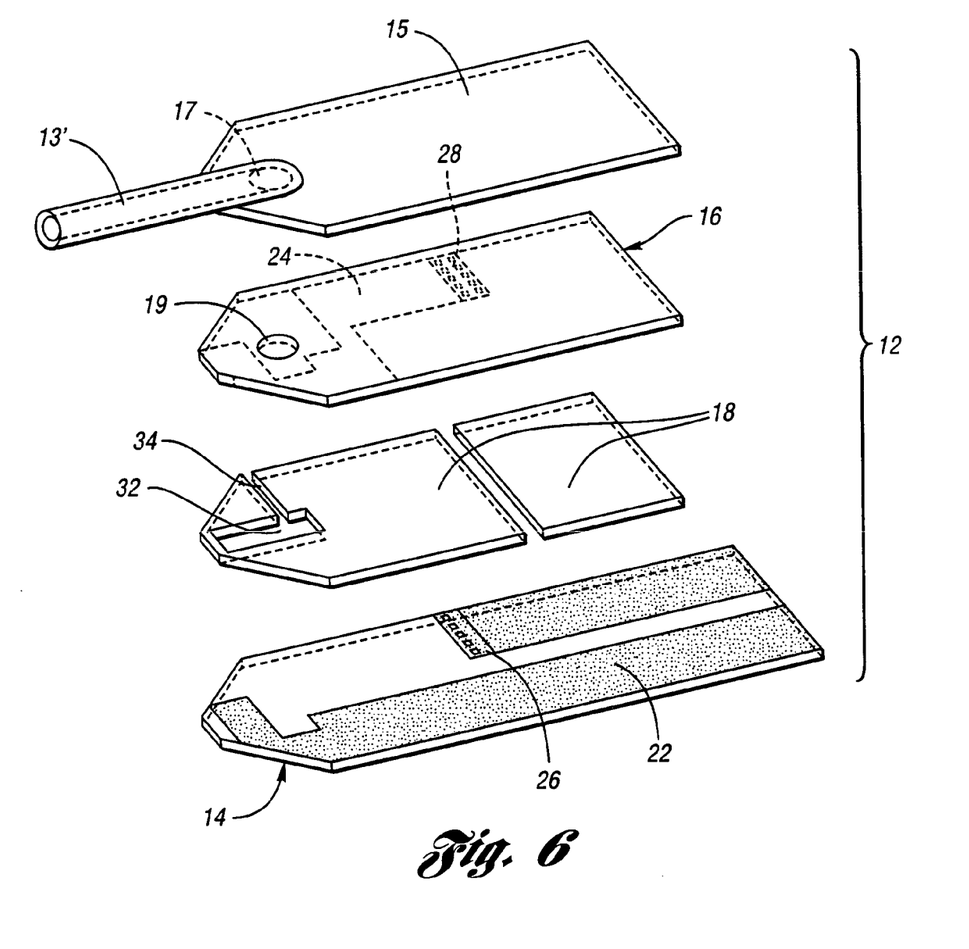
FIG. 6 is an exploded perspective view of the test probe of FIG. 5.
Figure 7:
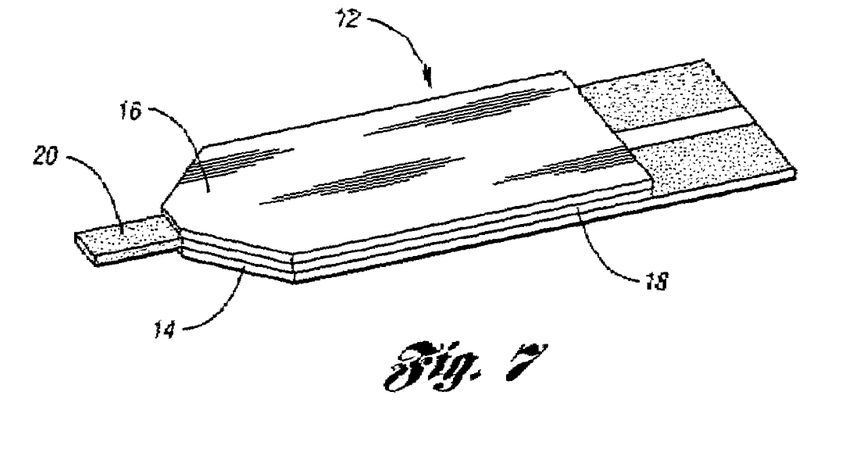
FIG. 7 is a perspective view of another alternative embodiment of the test probe according to the present invention.

With reference now to FIGS. 3–8, test probe 12 of the present invention includes a base plate 14, a cover plate 16, and a spacer 18 inserted therebetween. Test probe 12 has a sample inlet, as described below, which is arranged for obtaining the tear fluid sample via contact with the user's eye, and is preferably free of sharp edges so as to facilitate contact with the user's eye and lid margin. In a preferred embodiment, the sample inlet is constructed to extend outwardly from test probe 12 as shown in FIGS. 3–8 to further aid in obtaining the tear fluid sample. In the embodiment depicted in FIGS. 3 and 4, the sample inlet includes a capillary member 13 that protrudes from test probe 12, wherein opposed halves of member 13 are molded into each of base and cover plates 14, 16 such that member 13 is formed upon assembly of test probe 12. Capillary member 13 is placed in contact with the eye region and the tear fluid sample is drawn up into capillary member 13 by capillary action. FIGS. 5 and 6 illustrate an alternative capillary configuration, wherein a capillary member 13' is fully formed in an auxiliary plate 15 covering cover plate 16. Auxiliary plate 15 and cover plate 16 are provided with connection apertures 17 and 19, respectively, which are aligned upon assembly of test probe 12 such that the tear fluid sample can flow from capillary member 13' to spacer 18 and base plate 14. In another alternative embodiment depicted in FIGS. 7 and 8, the sample inlet can include a wicking membrane 20 for drawing the tear fluid sample into test probe 12. Wicking membrane 20 can be constructed from materials such as nitrous cellulose, filter paper, or the like. Of course, it is understood that test probe 12 may be used without capillary members 13, 13', wicking membrane 20, or the like and contact the eye region E directly to obtain the tear fluid sample.

Figure 8:
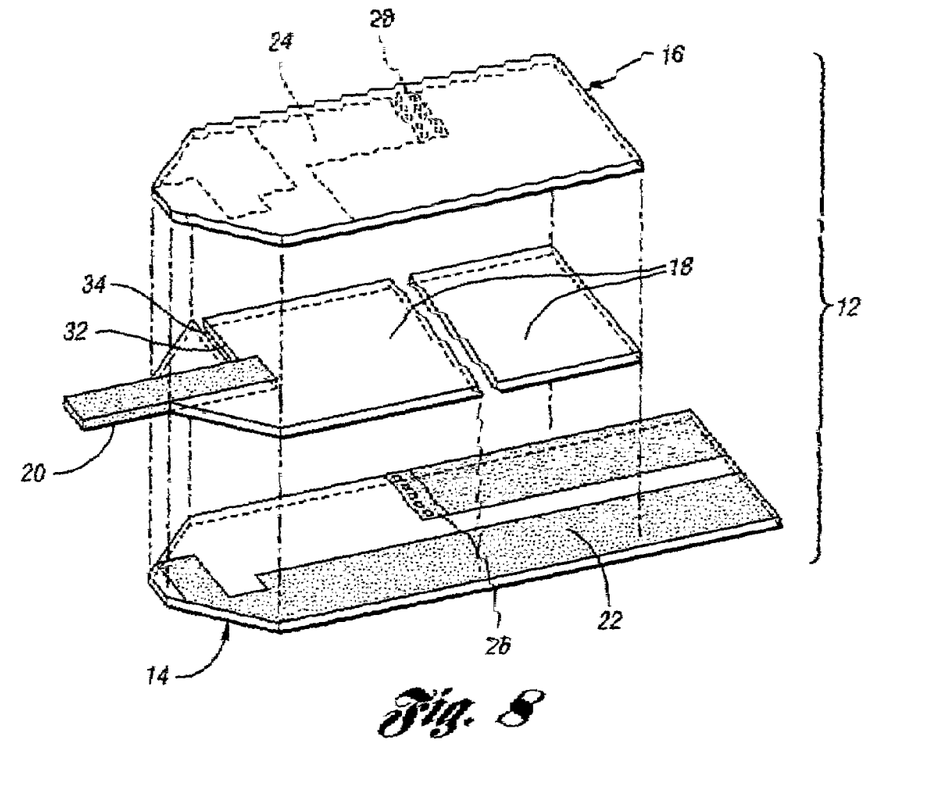
FIG. 8 is an exploded perspective view of the test probe of FIG. 7.

As shown in the exploded view of FIGS. 4, 6, and 8, base and cover plates 14, 16 of test probe 12 include an electrode system comprising a working electrode 22 and a reference electrode 24. Most preferably, the electrode system is of a converse-type in which working electrode 22 and reference electrode 24 are disposed on different plates 14, 16 in an opposed, spaced apart relationship. Such a converse configuration has been shown to allow for reduced sample volume and measurement time. Of course, other types of electrode configurations could also be utilized for carrying out the present invention.

With continuing reference to FIGS. 3–8, base plate 14 includes working electrode 22 and a first electrode connector 26 provided thereon, and cover plate 16 includes reference electrode 24 and a second electrode connector 28 provided on an underside thereof. Immobilized on working electrode 22 is an enzyme and an electron transfer mediator, as described below with reference to FIG. 9. A view window (not shown) may be provided in cover plate 16 to offer a visual indication of sample uptake into test probe 12. Base and cover plates 14, 16 are preferably constructed of ceramic, glass, or polymeric materials, most preferably an organic polymer of polyester, polyvinyl chloride, or polycarbonate. Working electrode 22, reference electrode 24, and electrode connectors 26, 28 are constructed using a conductive material, e.g., silver epoxy, silver/silver chloride, carbon, redox couples, or a modified conductive carbon paste containing a resin binder. These materials can be formed into electrodes 22, 24 and electrode connectors 26, 28 by a screen-printing method, an ink jet printing method, a vapor deposition method followed by etching, an adhesion of a conductive tape, or the like. Base plate 14 preferably extends rearwardly beyond cover plate 16 as shown for insertion into test apparatus 10 (see FIGS. 3, 5, and 7).

Referring again to FIGS. 4, 6, and 8, spacer 18 includes a channel 32 for introduction of the tear fluid sample into test probe 12 and a discharge passage 34. Due to capillary action, the tear fluid sample is introduced into channel 32 via the sample inlet, such as capillary members 13, 13' or wicking membrane 20, while any air or excess sample is discharged through discharge passage 34. The shape of the channel 32 aids in reducing the sample volume required for glucose concentration measurements. Spacer 18 is preferably constructed by pressing a double-sided adhesive film made of organic polymer comprising polyester, polyvinyl chloride, or polycarbonate onto the base, or screen-printing a layer of adhesive onto base plate 14 with the pattern shown in FIGS. 4, 6, and 8. Pressing cover plate 16 onto test probe 12, so as to align and connect electrode connectors 26, 28, completes the circuit and forms the assembled test probe 12 shown in FIGS. 3, 5, and 7. Test probe 12 can be constructed to be disposable for one time use, or alternatively can be constructed to be reusable. In the latter case, test probe 12 can be coded with an allowed number of uses or an expiration date after which it should be replaced.

In operation, the tear fluid sample obtained through contact of the sample inlet with a user's eye flows through channel 32 of spacer 18 and into contact with working electrode 22 on base plate 14 of test probe 12. As indicated above, working electrode 22 includes an enzyme and an electron transfer mediator immobilized thereon for reacting with glucose in the tear sample in order to determine its glucose concentration. The tear fluid volume required for the test is less than about 0.5 μl, although it is fully contemplated that the test probe could be constructed to accommodate a sample of larger volume. The test time is approximately 5 seconds.

Figure 9:
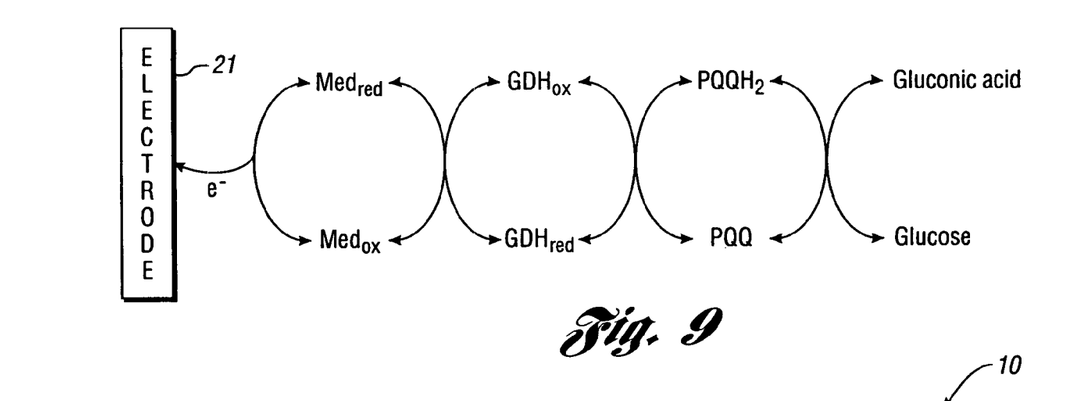
FIG. 9 is an illustration of the electrochemical reaction scheme of the test probe according to a preferred embodiment of the present invention.

For the method and apparatus of the present invention, the preferred electrochemical reaction schematic is depicted in FIG. 9, wherein glucose dehydrogenase (GDH) is utilized as the enzyme and a ruthenium complex is used as the electron transfer mediator (Med). Given the low level glucose measurements required for tear fluid, glucose dehydrogenase is preferred over glucose oxidase. The electron transfer mediator provided for working electrode 22 may include organometallic compounds (e.g., Fe, Os, Ru containing derivatives), ferrocene or its derivatives, ferricyanide, quinone or its derivatives, organic conducting salts, viologen, or other compounds. However, a ruthenium complex is preferred since both its oxidized and reduced states in aqueous solution are stable and reversible, the reduced mediator is non-reactive to oxygen, its formal potential is low enough to minimize the influence of interfering materials, the oxidation of the reduced mediator is not sensitive to pH, and it does not react with electrochemically interfering materials. As shown, pyrrolo-quinoline-quinone (PQQ) is preferably used as a coenzyme for glucose dehydrogenase in the reaction scheme of the present invention.

As shown in the reaction scheme of FIG. 9, glucose undergoes an enzymatic reaction wherein glucose is oxidized to gluconic acid by reducing glucose dehydrogenase ($GDH_{red}$). The reduced glucose dehydrogenase transfers an electron to the electron transfer mediator ($Med_{ox}$) and then returns to an initial state ($GDH_{ox}$). The consequently reduced mediator ($Med_{red}$) becomes reoxidized at the working electrode. The oxidation of the reduced mediator results in a redox current which is specifically related to the concentration of the glucose in the tear fluid sample.

Figure 10:
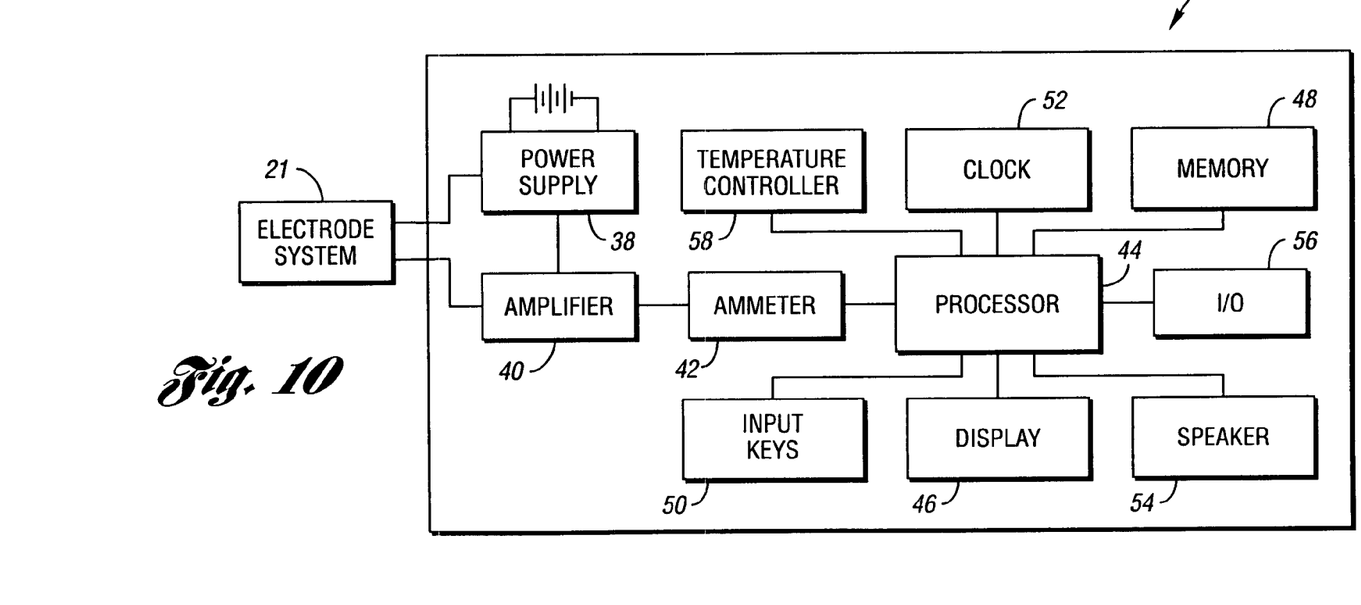
FIG. 10 is a schematic illustration of the electronic circuit and components of the test apparatus of the present invention.

Referring now to FIGS. 2 and 10, test apparatus 10 includes a port 36 for removably receiving test probe 12, and contains an electronic circuit and components (shown schematically in FIG. 10) for measuring the current resulting from the enzymatic reaction, similar to readers used for blood glucose analysis. After obtaining the tear fluid sample, which subsequently flows into contact with working electrode 22 via capillary action, a power supply 38 applies a voltage to electrode system 21 of test probe 12, which induces the series of electrochemical reactions for glucose described above. Electrode system 21 is in communication with an amplifier 40 such that the resultant current, which is directly proportional to tear glucose concentration, is amplified, detected by a sensor such as an ammeter 42 or the like, and subsequently translated to a value for tear glucose concentration by a processor 44. Processor 44 then correlates the determine tear glucose concentration with blood glucose concentration, such as by multiplication with a calibration factor, and the resulting value is displayed on an LCD display screen 46 (see also FIG. 2) provided on the test apparatus 10.

Still referring to FIG. 10, in a preferred embodiment, test apparatus 10 includes memory 48 for storing each glucose concentration value, along with the date, time of day, and possibly other input information for later reference by the user and his/her physician. Keys 50 (see also FIG. 2) are provided for user input and data recall purposes, and a clock 52 is provided in communication with processor 44. A speaker 54 can be provided for sounding a beep or the like when an adequate test sample volume has been obtained, advantageously providing the user with an audible indication that test apparatus 10 can be removed from contact with their eye region. Speaker 54 may additionally be used to indicate test completion. Test apparatus 10 can also be configured to upload glucose concentration data for access by a physician for remote monitoring purposes. For example, this can be accomplished via a standard I/O port 56 such as a USB or firewire port or the like, or by extracting a removable memory card (not shown) and reading the stored data via a standard format card reader. In addition, test apparatus 10 can include a temperature controller 58 for regulating the temperature of the enzymatic reaction.

In preliminary studies, the self-sampling method and apparatus of the present invention were evaluated. Each user learned the self-sampling method in a single session and repeated it without failure in multiple sessions. Significantly, neither tear insufficiency (dry eye) nor reflex tearing during self-sampling was found to have an effect on tear glucose concentration.

Figure 11:
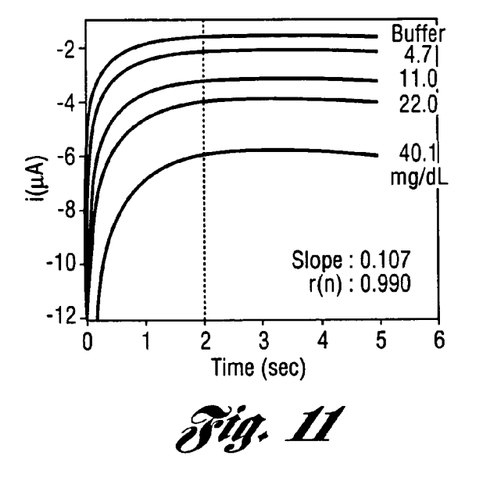
FIG. 11 is a graph of the dynamic response of current measured for a range of glucose concentrations in PBS using the apparatus of the present invention.
Figure 12:
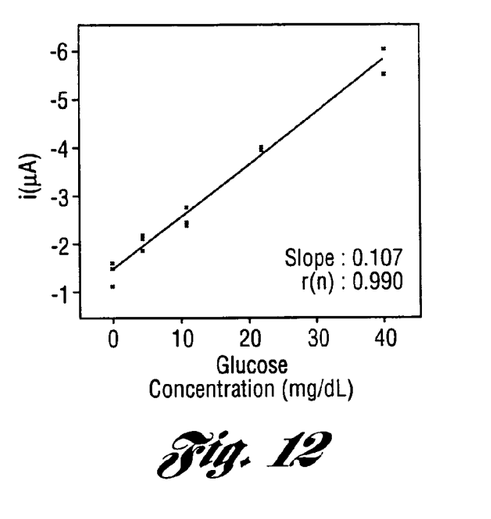
FIG. 12 is a graph of the calibration curve of currents measured for glucose concentrations from 0–40 mg/dL using the apparatus of the present invention.
Figure 13:
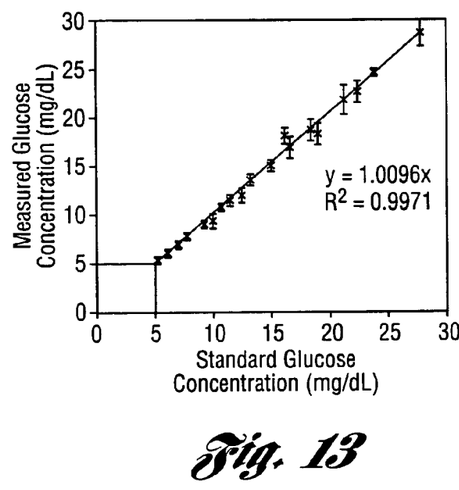
FIG. 13 is a graph depicting the precision and accuracy for glucose concentrations ranging from 0–28 mg/dL in a simulated tear matrix.
Figure 14:
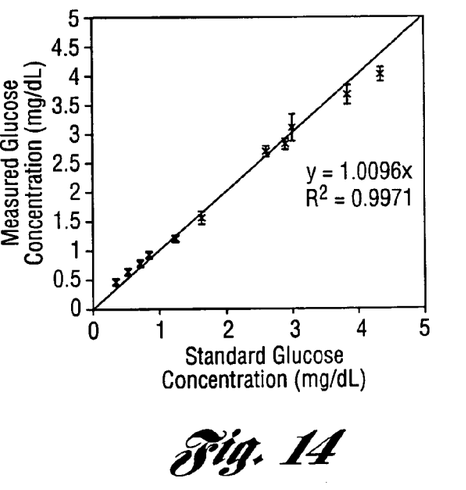
FIG. 14 is an enlarged portion of the graph of FIG. 13 depicting the precision and accuracy for low concentrations of glucose ranging from 0–5 mg/dL.

Glucose solutions in a range of concentrations equivalent to those reported for tears were tested using the apparatus of the present invention. The dynamic response of the apparatus to a range of concentrations of glucose in PBS is shown in FIG. 11, wherein the currents reach steady-state after approximately 2 seconds. A calibration curve was constructed for the range of concentrations of glucose from 0–40 mg/dL (FIG. 12) using solutions of glucose in a simulated tear matrix (0.01 M phosphate buffer containing 140 mM NaCl, 5 g/L of bovine serum albumin, pH 7.6). The results showed high accuracy and precision of glucose measurement, not only in the normal tear range, but also at levels up to 50% below normal. Accuracy and precision were tested with concentrations of the standard glucose solution from 0–28 mg/dL, n=5 (FIG. 13). As shown in FIG. 14, linearity persists at very low (anticipated hypoglycemic) glucose concentrations. Precision ranged from 0 to 8.7% CV. As shown in FIGS. 13 and 14, the apparatus according to the present invention is capable of detecting glucose concentrations less than about 20 mg/dL with a resolution of at least 5 mg/dL.

The method and apparatus of the present invention can be used to develop a correlational model between tear and blood concentrations of glucose, allowing the use of tear glucose readings in place of blood glucose readings to assess circulating levels of glucose in the body. Such a model may include covariate adjustment for demographic data such as subject age, gender, diabetic status, and perhaps other important terms, e.g. weight or body mass index, medications, and fasting status. Insight into the kinetics of the correlation between changes in blood and tear glucose can be assessed dynamically (i.e., as the level of blood glucose is increasing or decreasing) using the apparatus and method of the present invention. In addition, diurnal effects on tear glucose concentration can also be investigated.

In summary, prior to the development of the method and apparatus of the present invention, the approach of using tear glucose to monitor blood glucose has not been practical due to the low glucose concentration in tears and the submicroliter sample volumes available. The method and apparatus described herein are sensitive to the range of glucose concentrations present in tears, requires remarkably small sample volume, and uses a test apparatus that permits direct self-sampling of tears. Importantly, the test apparatus 10 allows for the sampling and testing of tear fluid sample with a single device, eliminating any need for intermediate handling of tears. By overcoming previous limitations, the method and apparatus of the present invention provide the capability to measure tear glucose, and therefore monitor blood glucose, in a simple, clinically practical manner.

The method and apparatus described herein offer a replacement to current patient direct measurement of blood glucose levels which require a finger stick to obtain a blood sample. In the medical management of diabetes, the glucose level is the essential information required for decisions on when, how much, and what type of insulin should be administered. Due to their completely noninvasive nature, the method and apparatus of the present invention could significantly improve the quality of medical care of diabetes through easily repeated testing to prevent hypoglycemia, the limiting factor in the management of insulin-dependent diabetes mellitus.

Although the measurement of glucose concentration in tears has been described herein, it is understood that the present invention provides a method and apparatus for obtaining and evaluating a tear fluid sample that can be used to determine the concentration of any substance in blood which also manifests a concentration in tears including, but not limited to, ascorbic acid, uric acid, albumin, plasma ions, and cholesterol as well as foreign substances such as drugs.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for determining the concentration of a substance in blood, the method comprising:
   providing a test apparatus having a housing and a test probe received therein;
   receiving a tear fluid sample via engagement of the test probe with an eye region of a user while the test probe is received within the test apparatus;
   processing the tear fluid sample using the test apparatus to determine a tear substance concentration; and
   correlating the determined tear substance concentration with a blood substance concentration.

2. The method according to claim 1, wherein the substance includes glucose.

3. The method according to claim 1, wherein receiving the tear fluid sample includes a user self-sampling the tear fluid sample from his eye region.

4. The method according to claim 1, wherein receiving the tear fluid sample includes engaging a lower lid region and obtaining tear fluid from a tear meniscus.

5. The method according to claim 1, further comprising displaying the blood substance concentration.

6. The method according to claim 1, further comprising storing the blood substance concentration.

7. The method according to claim 1, wherein the test probe includes a capillary member.

8. The method according to claim 1, wherein the test probe includes a wicking membrane.

9. The method according to claim 1, wherein the test probe includes an enzyme for reacting with the substance in the tear fluid sample.

10. The method according to claim 9, wherein the enzyme includes glucose dehydrogenase.

11. The method according to claim 9, wherein the test probe includes an electrode system provided therein, and wherein processing the tear fluid sample includes applying a voltage to the electrode system to induce an electrochemical reaction of the enzyme and the substance in the tear fluid sample, and detecting a current produced by the electrochemical reaction from which the tear substance concentration is determined.

12. The method according to claim 1, wherein receiving the tear fluid sample includes obtaining a tear fluid sample of less than about 0.5 µL.

13. The method according to claim 1, wherein a test time is about 5 seconds.

14. The method according to claim 1, wherein the test apparatus is capable of detecting glucose concentrations less than about 20 mg/dL with a resolution of at least 5 mg/dL.

15. The method according to claim 1, wherein the test probe is removable from the housing.

16. The method according to claim 1, wherein the housing is generally pen-shaped.

17. The method according to claim 1, further comprising providing an audible indication to the user.

18. A method for determining glucose concentration in a tear fluid sample, the method comprising:
provide a test apparatus having a housing and a test probe received therein, the test probe arranged for contacting an eye region of a user;
receiving a tear fluid sample via engagement of the test probe with an eye region of a user while the test probe is received within the test apparatus; and
processing the tear fluid sample using the test apparatus to determine the glucose concentration in the tear fluid sample.

19. The method according to claim 18, wherein receiving the tear fluid sample includes a user self-sampling the tear fluid sample from his eye region.

20. The method according to claim 18, wherein the test apparatus includes an enzyme for reacting with glucose in the tear fluid sample.

21. The method according to claim 20, wherein the enzyme include glucose dehydrogenase.

22. The method according to claim 18, wherein receiving the tear fluid sample includes obtaining a tear fluid sample of less than about 0.5 µL.

23. The method according to claim 18, wherein a test time is about 5 seconds.

24. The method according to claim 18, wherein the test apparatus is capable of detecting glucose concentrations less than about 20 mg/dL with a resolution of at least 5 mg/dL.

25. The method according to claim 18, wherein the test probe is removable from the housing.

26. The method according to claim 18, wherein receiving the tear fluid sample includes a user self-sampling the tear fluid sample from his eye region.

27. The method according to claim 18, further comprising displaying the tear glucose concentration.

28. The method according to claim 18, further comprising storing the tear glucose concentration.

29. The method according to claim 18, wherein the test probe includes a capillary member.

30. The method according to claim 18, wherein the test probe includes a wicking membrane.

31. The method according to claim 18, wherein the housing is generally pen-shaped.

32. The method according to claim 18, further comprising providing an audible indication to the user.

33. A method for determining blood glucose concentration, the method comprising:
providing a test apparatus including a sample portion, the sample portion having an enzyme provided therein;
receiving a tear fluid sample via engagement of the sample portion with an eye region of a user, wherein a volume of the tear fluid sample is less than about 0.5 µL;
reacting the tear fluid sample with the enzyme to generate a signal related to the tear glucose concentration;
processing the signal using the test apparatus to obtain a blood glucose concentration corresponding to the tear glucose concentration; and
providing an output indicative of the blood glucose concentration.

34. The method according to claim 33, wherein receiving the tear fluid sample includes a user self-sampling the tear fluid sample from his eye region.

35. The method according to claim 14, wherein the sample portion includes an inlet extending outwardly therefrom.

36. The method according to claim 35, wherein the inlet includes a capillary member.

37. The method according to claim 35, wherein the inlet includes a wicking membrane.

38. The method according to claim 14, wherein the enzyme includes glucose dehydrogenase.

39. The method according to claim 38, wherein the sample portion includes pyrrolo-quinoline-quinone as a coenzyme.

40. The method according to claim 14, wherein the sample portion includes an electron transfer mediator.

41. The method according to claim 14, wherein the electron transfer mediator includes a ruthenium complex.

42. The method according to claim 40, wherein the sample portion includes a base plate, a cover plate, and a spacer disposed between and joining the base and cover plates, the base and cover plates including a converse-type electrode system, wherein processing the tear fluid sample includes applying a voltage to the electrode system to induce an electrochemical reaction of the enzyme and the electron transfer mediator with glucose in the tear fluid sample and generate a current related to tear glucose concentration.

43. The method according to claim 42, further comprising amplifying the generated current.

44. The method according to claim 42, wherein processing the signal includes determining a tear glucose concentration from the generated current and multiplying the tear glucose concentration by a calibration factor to determine the corresponding blood glucose concentration.

45. The method according to claim 33, wherein a test time is about 5 seconds.

46. The method according to claim 33, wherein the test apparatus is capable of detecting glucose concentrations less than about 20 mg/dL with a resolution of at least 5 mg/dL.

47. The method according to claim 33, wherein the sample portion is removable from the test apparatus.

48. The method according to claim 33, wherein receiving the tear fluid sample includes a user self sampling the tear fluid sample from his eye region.

49. The method according to claim 33, wherein providing an output includes displaying the blood glucose concentration.

50. The method according to claim 33, further comprising storing the blood glucose concentration.

51. The method according to claim 33, wherein the housing is generally pen-shaped.

52. The method according to claim 33, further comprising providing an audible indication to the user.

* * * * *

UNITED STATES PATENT AND TRADEMARK OFFICE
CERTIFICATE OF CORRECTION

PATENT NO. : 7,133,712 B2  Page 1 of 1
APPLICATION NO. : 10/404702
DATED : November 7, 2006
INVENTOR(S) : Bruce E. Cohan et al.

It is certified that error appears in the above-identified patent and that said Letters Patent is hereby corrected as shown below:

Column 12, Line 6, Claim 35:

Delete "14" and insert therefor -- 33 --.

Column 12, Line 14, Claim 38:

Delete "14" and insert therefor -- 33 --.

Column 12, Line 20, Claim 40:

Delete "14" and insert therefor -- 33 --.

Column 12, Line 22, Claim 41:

Delete "14" and insert therefor -- 33 --.

Signed and Sealed this

Sixth Day of February, 2007

JON W. DUDAS
*Director of the United States Patent and Trademark Office*